(12) United States Patent  
Hajianpour

(10) Patent No.: US 7,169,149 B1  
(45) Date of Patent: Jan. 30, 2007

(54) DEVICE FOR EXTERNAL FIXATION OF A PROXIMAL FRACTURE OF THE ULNA WITH A CLAMPED MEDULAR PIN AND MULTIPLE CLAMPED PINS HOLDING BONE FRAGMENTS

(75) Inventor: Mohammed Ali Hajianpour, Coral Springs, FL (US)

(73) Assignee: Phoenix Orthopaedic Corporation, Sunrise, FL (US)

( * ) Notice: Subject to any disclaimer, the term of this patent is extended or adjusted under 35 U.S.C. 154(b) by 526 days.

(21) Appl. No.: 10/626,357

(22) Filed: Jul. 24, 2003

(51) Int. Cl.  
*A61B 17/56* (2006.01)  
*A61B 17/58* (2006.01)

(52) U.S. Cl. .......................... 606/54; 606/57; 606/59; 606/60

(58) Field of Classification Search .......... 606/53–59, 606/62, 64, 60, 63, 65, 68  
See application file for complete search history.

(56) References Cited

U.S. PATENT DOCUMENTS

| | | | |
|---|---|---|---|
| 3,763,855 A | 10/1973 | McAtee | |
| 3,877,424 A | 4/1975 | Murray | |
| 4,212,294 A | 7/1980 | Murphy | |
| 5,057,110 A | 10/1991 | Kranz et al. | |
| 5,102,411 A | 4/1992 | Hotchkiss et al. | |
| 5,190,544 A * | 3/1993 | Chapman et al. | 606/69 |
| 5,545,162 A | 8/1996 | Huebner | |
| 5,549,609 A * | 8/1996 | Frankel et al. | 606/64 |
| 6,080,159 A * | 6/2000 | Vichard | 606/64 |
| 6,152,935 A | 11/2000 | Marsh et al. | |
| 6,197,027 B1 | 3/2001 | Hajianpour | |
| 6,514,253 B1 * | 2/2003 | Yao | 606/53 |
| 6,585,736 B2 | 7/2003 | Hajianpour | |

* cited by examiner

*Primary Examiner*—Pedro Philogene  
(74) *Attorney, Agent, or Firm*—Ronald V. Davidge

(57) ABSTRACT

A device for external fixation of a fracture of the proximal end of the ulna includes an frame having a distal elongated portion extending below the ulna, holding a number of pins extending upward into the shaft portion, and a proximal portion extending rearward, and upward around the proximal end of the ulna, holding a medullar pin extending into a medullar channel and a number of pins extending into fragments of the fractured ulna.

13 Claims, 2 Drawing Sheets

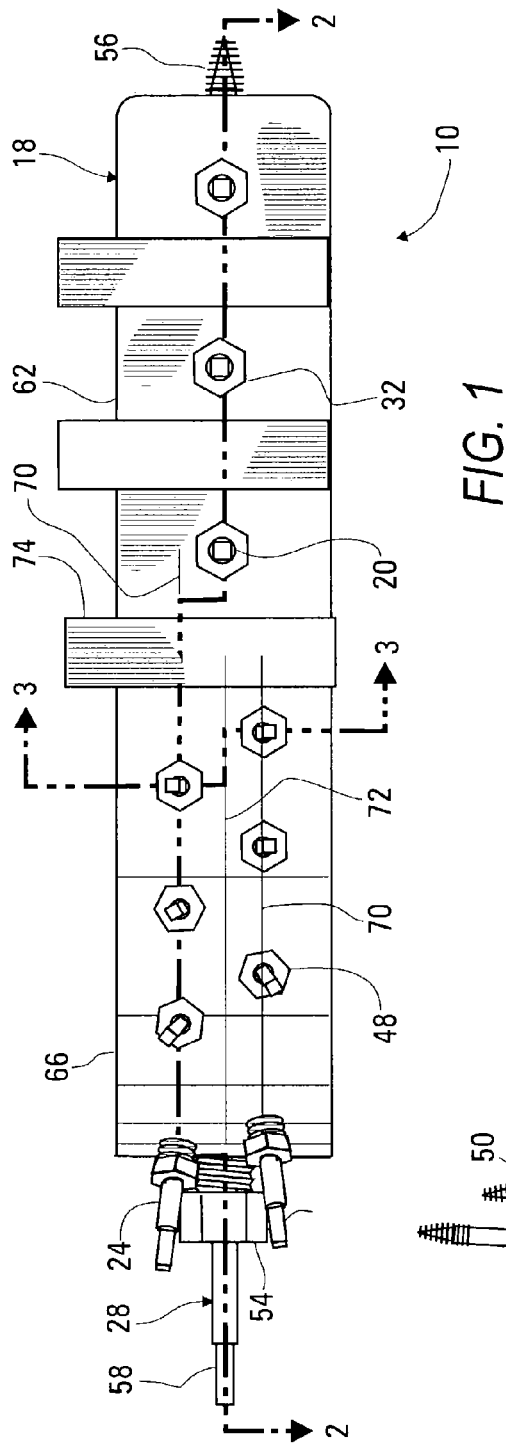
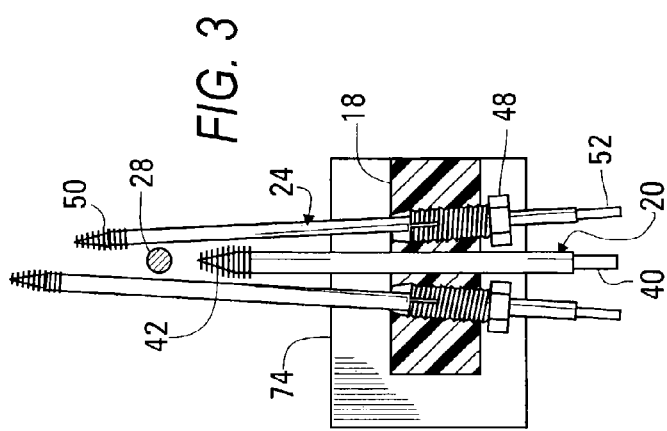

DEVICE FOR EXTERNAL FIXATION OF A PROXIMAL FRACTURE OF THE ULNA WITH A CLAMPED MEDULLAR PIN AND MULTIPLE CLAMPED PINS HOLDING BONE FRAGMENTS

BACKGROUND OF THE INVENTION

1. Field of the Invention

This invention relates to external fixation devices for holding bone fragments in place, and, more particularly, to such devices for holding such fragments at a proximal end of the ulna.

2. Summary of the Background Art

The patent literature includes a number of patents describing assemblies including medullar pins or screws to be installed to extend longitudinally within the ulna from its proximal end at the elbow, providing for the positive fixation of fractures of the ulna at or near the elbow joint. For example, U.S. Pat. Nos. 3,763,855 and 4,212,294 describe versions an elongated assembly including a first element that is inserted from the side through the cortex of the bone into the soft central channel of the bone below the fracture and a second element in the form of a flexible medullar pin extending through the transverse hole in the first element, with external threads of the medullar pin engaging threads within the transverse hole. In another such example, U.S. Pat. No. 5,549,609 describes a bone fixation assembly for fracture(s) of the upper ulna, the ulna having an olecranon and a proximate end, comprising a elongated medullary pin and a head member. The elongated medullar pin has a longitudinal axis and distal and proximal ends and at least one aperture at its distal end for transverse locking screw(s). The head member is disposed at the proximal end of the pin for transmitting force to the olecranon along the longitudinal axis of the pin as the head member is tightened. The head member comprising at least one inwardly extending, projecting, pointed portion.

U.S. Pat. No. 5,057,110 describes an intramedullar nail for the treatment of fractures of long tubular bones, made of a shaft having a nail tip and at least one fixation screw. A portion of the nail tip is made of absorbable material. The fixation screws penetrate the bone and a section of the nail, causing the bone and nail to be attached.

U.S. Pat. Nos. 5,102,411 and 6,152,925 describe versions of an external fixation device for use at the elbow, with a hinge mechanism aligned with the elbow, an upper assembly extending along the upper arm from the hinge assembly to be fastened into the bone therein by one or more bone pins, and a lower assembly extending along the lower arm from the hinge assembly to be fastened into a bone therein by one or more bone pins.

Other patents describe external fixation devices installed to extend along a broken bone with pins from the device extending into the side of the bone, at least on both sides of the fracture. For example, U.S. Pat. No. 3,877,424 describes a method comprising inserting at least one pin in each major fragment of bone with a portion of the pins extending above the skin surface, drawing the pins toward one another and applying a bridge to the pins to hold them in place under compression parallel to the bone being repaired, together with an apparatus including at least two elongated pins adapted to be inserted at one end into the bone on opposite sides of a fracture, bridge means engaging the other ends and compression means acting on the pins generally parallel to the bone. U.S. Pat. Nos. 5,545,162, 6,197,027, and 6,585,736 describe external fixation devices particularly configured for use with a fractured distal radius.

SUMMARY OF THE INVENTION

According to a first aspect of the invention, an external fixation device is provided for holding a number of pins extending into a fractured bone of a patient. The external fixation device includes a frame, a number of shaft attachment pins in shaft attachment pin clamps for attachment within a shaft portion of the fractured bone, a number of fragment attachment pins in fragment attachment pin clamps for attachment within fragments of the fractured bone, a medullar pin in a medullar clamp for attachment within a medullar channel of the fractured bone, and a frame. The frame includes an elongated distal portion and a proximal portion extending from a proximal end of the elongated portion upward and in the first direction, extending rearward and upward from the distal portion. The number of shaft attachment pin clamps extend along the elongated portion. The shaft attachment pin clamps hold the shaft attachment pins to extend upward from the flat surface. The number of fragment attachment pin clamps extend along the proximal portion, holding the fragment attachment pins to extend inward. The medullar pin clamp is disposed at an upper end of the curved portion, holding the medullar pin to extend over the distal end portion of the frame.

According to another aspect of the invention, a method is provided for external fixation of a proximal fracture of the ulna within a patient. The method includes surgically installing a medullar pin, surgically installing a number of shaft attachment pins, and surgically installing a number of fragment attachment pins. The medullar pin is installed to extend through a medullar pin clamp within an external fixation device and through a distal end of the fractured bone into a medullar channel within the fractured bone. The shaft attachment pins are installed to extend through a number of shaft attachment pin clamps within an elongated distal portion of a frame of the external fixation device into a shaft portion of the bone, with each of the shaft attachment pins extending upward. The fragment attachment pins are installed to extend through a number of fragment attachment pin clamps within a proximal portion of the fixture, into fragments near the end of the bone.

BRIEF DESCRIPTION OF THE FIGURES

FIG. 1 is a bottom plan view of an external fixation device built in accordance with the invention;

FIG. 3 is a transverse cross-sectional view of the fixture of FIG. 1, taken as indicated by section lines 3—3 therein.

DETAILED DESCRIPTION OF THE INVENTION

Figure 2:
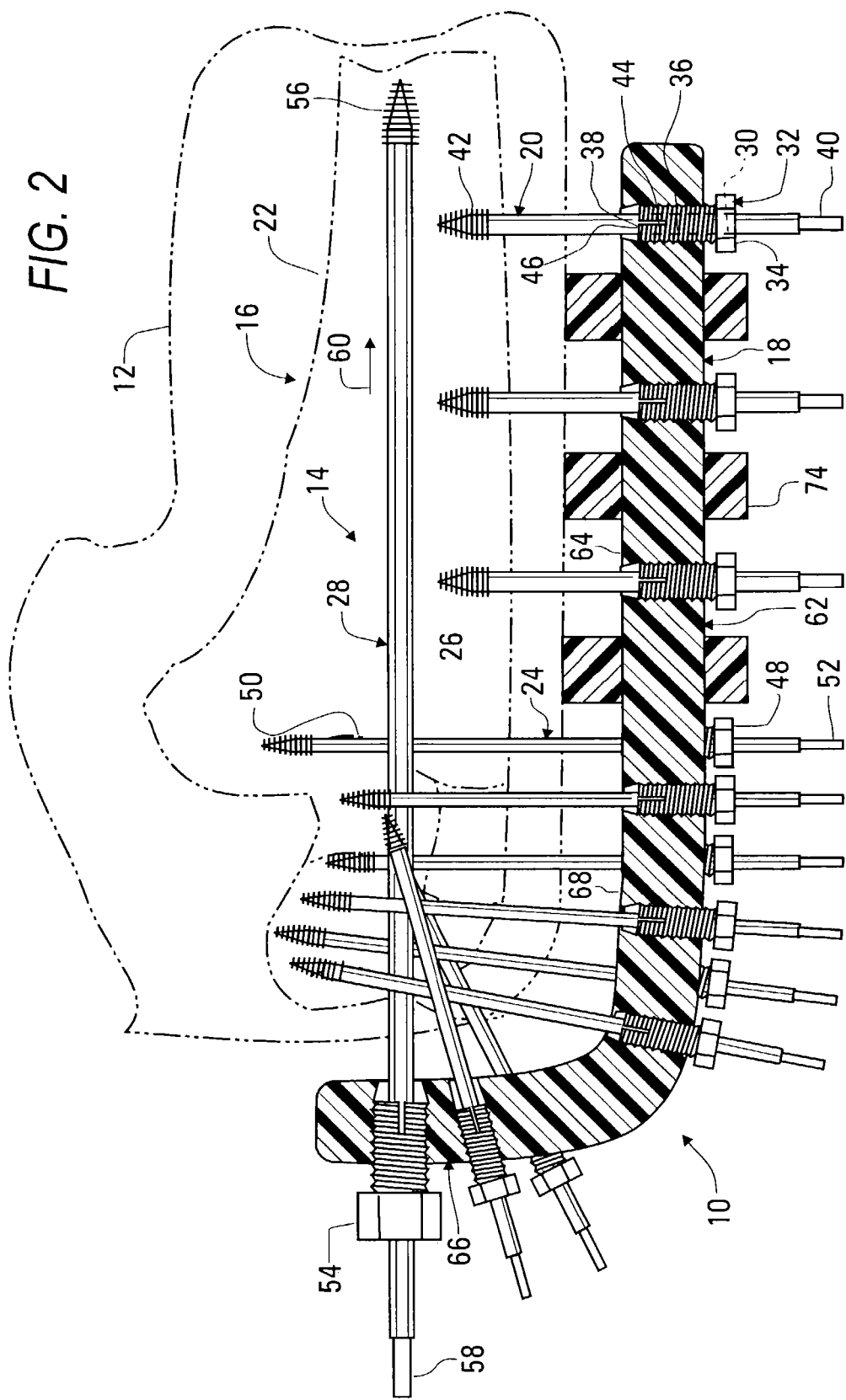
FIG. 2 is a longitudinal cross-sectional view of the fixture of FIG. 1, taken as indicated by section lines 2—2 therein, shown as installed on the arm of a patient.

A device 10 for external fixation or a proximal fracture of the ulna will now be discussed, with reference being made to FIG. 1, a bottom plan view of the fixation device 10, to FIG. 2, a longitudinal cross section thereof, taken as indicated by section lines 2—2 in FIG. 1, and additionally to FIG. 3, a transverse cross section thereof, taken as indicated by section lines 3—3 in FIG. 1. FIG. 2 additionally shows the fixation device 10 as installed on the arm 12 of a patient with pins 14 from the fixture extending into the ulna. The arm 12 and ulna 16 are shown in phantom lines.

The fixture 10 includes a frame 18, a number of shaft attachment pins 20 provided for installation into the shaft portion 22 of the fractured ulna 16, a number of fragment attachment pins 24 provided for installation into proximal fragments 26 of the fractured ulna 16, and a medullar pin 28 to be fastened within the central medullar channel of the fractured ulna 16. Each of the pins 20, 24, 28 is individually clamped in place within the frame 18. For example, each of the shaft attachment pins 20 extends through a hole 30 within a shaft pin clamping screw 32 including a noncircular head 34 and an externally threaded portion 36 extending to a slotted end 38. The shaft pin 20 includes a non-circular end 40 extending outward from the frame 18 and a helically threaded end 42 extending inward from the frame 18. The frame 18 includes an internally threaded hole 44 extending to a tapered portion 46.

The shaft attachment pin 20 is surgically installed within the arm 22 and the bone 16, with the helical threads 42 being driven into engagement within the bone 16 by rotation of the pin 12 with a powered or manual screw-driving tool engaging the noncircular end portion 40 of the pin 20. Then, the shaft pin clamping screw 32 is rotated into engagement to clamp the screw 20 extending within the hole 30 as segments in the slotted end 38 of the clamping screw 32 are pushed inward against the screw 10 by contact with the tapered hole portion 46.

Each of the fragment attachment pins 24 extends within a fragment attachment clamping screw 48, which is used in a manner similar to the shaft pin clamping screw 32 to clamp the fragment attachment pin 24 in place within the fixture 10. Like the shaft attachment pins 20, the fragment attachment pins 24 each have a helically threaded portion 50 and a non-circular drive end 52 to be used as the pins 24 are surgically installed to support various bone fragments 26.

The medullar screw 28 extends in a first direction, as indicated by arrow 60, from a medullar clamping screw 54, which is used in a manner similar to the shaft pin clamping screw 32 to clamp the medullar pin 24 in place within the fixture 10. Like the shaft attachment pins 20, the medullar pin 24 has a helically threaded portion 56 and a non-circular drive end 58 to be used as the pin 28 is surgically installed.

The frame 18 includes a distal elongated portion 62, having a flat inner surface 64 extending parallel to the medullar screw 28 and offset therefrom, and a proximal potion 66, extending rearward, opposite the direction of arrow 60, and upward from the distal elongated portion 62. The curved portion 66 has an inner surface 68 extending from the flat inner surface 64. Each of the fragment attachment pins 24 is held by a fragment attachment pin clamping screw to extend upward.

FIG. 3 is a transverse cross-sectional view of the external fixation device 10, being taken as indicated by section lines 3—3 in FIG. 1. The fragment attachment screws 24 are preferably disposed in a staggered pattern along a pair of spaced-apart lines 70 extending longitudinally along the inner surface 68, and are additionally held to extend inward and toward a line 72 extending between the spaced-apart lines. The number of fragment attachment screws 24 to be used is determined by the nature of the bone fracture. Except for the pins 20, 24, 28, components of the fixation device 10 are preferably composed of molded thermoplastic resins that are transparent to X-rays, so that fluoroscopic examination can be employed during the surgical installation of pins 20, 24, 28, aiding in the maneuvering of bone fragments 26 into appropriate locations.

Preferably, the fixation device 10 additionally includes a number of spacing blocks 74, which are employed to keep the frame 18 spaced away from the arm 12 of the patient during the installation and adjustment of the screws 20, 24, 28. After this process is completed, the spacing blocks 74 are slid off and discarded. While the invention has been described in its preferred embodiment with some degree of particularity, it is understood that this description has been given only by way of example, and that many variations can be made without departing from the spirit and scope of the invention, as defined by the appended claims.

What is claimed is:

1. An external fixation device for the fixation of a proximal fracture of an ulna within a patient, wherein said external fixation device includes:

a frame including an elongated distal portion, having an inner surface facing upward, and a proximal portion extending rearward and upward from said distal portion, having an inner surface facing upward and forward;

a plurality of shaft attachment pins for attachment within a shaft portion of said fractured bone;

a plurality of shaft attachment pin clamps extending along said elongated distal portion, wherein said shaft attachment pin clamps clamp said shaft attachment pins within said elongated distal portion to extend upward from said elongated distal portion;

a plurality of fragment attachment pins for attachment within fragments of said fractured bone;

a plurality of fragment attachment pin clamps extending along said proximal portion, wherein said fragment attachment pin clamps clamp said fragment attachment pins within said proximal portion to extend upward from said proximal portion;

a medullar pin for attachment within a medullar channel of said fractured bone; and a medullar pin clamp disposed within an upper end of said proximal portion, wherein said medullar pin clamp clamps said medullar pin within said upper end of said proximal portion to extend above said elongated distal portion.

2. The external fixation device of claim 1, wherein said shaft attachment pins are held within said shaft attachment pin clamps to be disposed along a line extending toward a distal end of said external fixation device.

3. The external fixation device of claim 1, wherein said fragment attachment pins are held within said fragment attachment pin clamps to be disposed along a pair of spaced apart lines extending longitudinally along said proximal portion.

4. The external fixation device of claim 3, wherein said fragment attachment pins are held within said fragment attachment pin clamps to extend inward from said proximal portion of said frame and toward a line between said spaced apart lines extending between proximal and distal ends of said external fixation device.

5. The external fixation device of claim 1, wherein one or more of said fragment attachment pin clamps each hold a fragment pin to extend inward and upward from an upstanding end of said proximal portion.

6. An external fixation device for the fixation of a proximal fracture of an ulna within a patient, wherein said external fixation device includes:

a frame including an elongated distal portion having an inner surface facing upward, wherein said elongated distal portion includes a plurality of shaft pin attachment holes, each including an internally threaded portion and a tapered portion extending from an end of said internally threaded portion to said inner surface of said elongated distal portion, and a proximal portion extending rearward and upward from said distal portion, having an inner surface facing upward and forward, wherein said proximal portion includes a plurality of fragment pin attachment holes, each including an internally threaded portion and a tapered portion extending from an end of said internally threaded portion to said inner surface of said proximal portion, and a medullar pin attachment hole, including an internally threaded portion and a tapered portion extending from an end of said internally threaded portion to said inner surface of said proximal portion;

a plurality of shaft attachment pins for attachment within a shaft portion of said fractured bone;

a plurality of shaft attachment pin clamps extending along said elongated distal portion, wherein said shaft attachment pin clamps hold said shaft attachment pins to extend upward from said elongated distal portion;

a plurality of fragment attachment pins for attachment within fragments of said fractured bone;

a plurality of fragment attachment pin clamps extending along said proximal portion, wherein said fragment attachment pin clamps hold said fragment attachment pins to extend upward from said proximal portion;

a medullar pin for attachment within a medullar channel of said fractured bone; and a medullar pin clamp disposed within an upper end of said proximal portion, wherein said medullar pin clamp holds said medullar pin to extend above said elongated distal portion, wherein each of said pin clamps includes an externally threaded portion including longitudinally extending slots at a first end, a non-circular head at an end opposite said first end, and a hole extending through said pin clamp for holding a pin, and wherein said first end of said threaded portion clamps a pin extending through said hole within said pin clamp as said pin clamp is driven into engagement with said tapered portion.

7. An external fixation device for the fixation of a proximal fracture of an ulna within a patient, wherein said external fixation device includes:

a frame including an elongated distal portion, having an inner surface facing upward, and a proximal portion extending rearward and upward from said distal portion, having an inner surface facing upward and forward;

a plurality of shaft attachment pins for attachment within a shaft portion of said fractured bone;

a plurality of shaft attachment pin clamps extending along said elongated distal portion, wherein said shaft attachment pin clamps hold said shaft attachment pins to extend upward from said elongated distal portion;

a plurality of fragment attachment pins for attachment within fragments of said fractured bone;

a plurality of fragment attachment pin clamps extending along said proximal portion, wherein said fragment attachment pin clamps hold said fragment attachment pins to extend upward from said proximal portion;

a medullar pin for attachment within a medullar channel of said fractured bone;

a medullar pin clamp disposed within an upper end of said proximal portion, wherein said medullar pin clamp holds said medullar pin to extend above said elongated distal portion; and a plurality of removably attached spacers holding said frame spaced away from said patient during installation of said pins.

8. A method for external fixation of a proximal fracture of an ulna within a patient, comprising:

surgically installing a medullar pin to extend through a medullar pin clamp within a proximal end of an external fixation device and through proximal end of said ulna into a medullar channel within said ulna;

surgically installing a plurality of shaft attachment pins to extend through a plurality of shaft attachment pin clamps within an elongated distal portion of a frame of said external fixation device into a shaft portion of said ulna, wherein each of said shaft attachment pins extends upward; and surgically installing a plurality of fragment attachment pins to extend through a plurality of fragment attachment pin clamps within a proximal portion of said external fixation device, to extend upward and inward within fragments near said proximal end of said ulna, wherein a surgical installation of each pin includes clamping said pin to said external fixation device.

9. The method of claim 8, wherein said shaft attachment pins are held by said shaft attachment pin clamps to be disposed along a line extending between proximal and distal ends of said external fixation device.

10. The method of claim 8, wherein said fragment attachment pins are held within said fragment attachment pin clamps to be disposed along a pair of spaced apart lines extending longitudinally along said proximal portion.

11. The method of claim 10, wherein said fragment attachment pins are held within said fragment attachment pin clamps to extend into said fragments and toward a line between said spaced apart lines extending longitudinally along said proximal portion.

12. A method for external fixation of a proximal fracture of an ulna within a patient, comprising:

surgically installing a medullar pin to extend through a medullar pin clamp within a proximal end of an external fixation device and through proximal end of said ulna into a medullar channel within said ulna;

surgically installing a plurality of shaft attachment pins to extend through a plurality of shaft attachment pin clamps within an elongated distal portion of a frame of said external fixation device into a shaft portion of said ulna, wherein each of said shaft attachment pins extends upward; and surgically installing a plurality of fragment attachment pins to extend through a plurality of fragment attachment pin clamps within a proximal portion of said external fixation device, to extend upward and inward within fragments near said proximal end of said ulna, wherein a surgical installation of each pin includes rotating a clamping screw forming a pin clamp having said pin extending through a hole within said clamping screw to drive segments of a slotted end of said clamping screw together to hold said pin as said slotted end of said clamping screw is driven into engagement with a tapered hole within said frame.

13. A method for external fixation of a proximal fracture of an ulna within a patient, comprising:

surgically installing a medullar pin to extend through a medullar pin clamp within a proximal end of an external fixation device and through proximal end of said ulna into a medullar channel within said ulna;

surgically installing a plurality of shaft attachment pins to extend through a plurality of shaft attachment pin clamps within an elongated distal portion of a frame of said external fixation device into a shaft portion of said ulna, wherein each of said shaft attachment pins extends upward;

surgically installing a plurality of fragment attachment pins to extend through a plurality of fragment attachment pin clamps within a proximal portion of said external fixation device, to extend upward and inward within fragments near said proximal end of said ulna, and removing a plurality of spacers from said external fixation device, wherein said spacers hold said frame spaced away from said patient.

* * * * *